(12) United States Patent
Alexandersson

(10) Patent No.: US 11,033,686 B2
(45) Date of Patent: Jun. 15, 2021

(54) ADMINISTRATION MECHANISM FOR A MEDICAMENT DELIVERY DEVICE

(71) Applicant: SHL MEDICAL AG, Zug (CH)

(72) Inventor: Oscar Alexandersson, Haninge (SE)

(73) Assignee: SHL MEDICAL AG, Zug (CH)

(*) Notice: Subject to any disclaimer, the term of this patent is extended or adjusted under 35 U.S.C. 154(b) by 333 days.

(21) Appl. No.: 16/301,337

(22) PCT Filed: Mar. 29, 2017

(86) PCT No.: PCT/EP2017/057401
§ 371 (c)(1),
(2) Date: Nov. 13, 2018

(87) PCT Pub. No.: WO2017/198383
PCT Pub. Date: Nov. 23, 2017

(65) Prior Publication Data
US 2019/0192776 A1    Jun. 27, 2019

(30) Foreign Application Priority Data
May 18, 2016 (SE) .................................... 1650673-5

(51) Int. Cl.
*A61M 5/20* (2006.01)
*A61M 5/28* (2006.01)
*A61M 5/32* (2006.01)

(52) U.S. Cl.
CPC .......... *A61M 5/2033* (2013.01); *A61M 5/282* (2013.01); *A61M 5/326* (2013.01); *A61M 2005/3267* (2013.01)

(58) Field of Classification Search
CPC .... A61M 5/2033; A61M 5/282; A61M 5/326; A61M 2005/3267

(Continued)

(56) References Cited

U.S. PATENT DOCUMENTS

2008/0015520 A1   1/2008   Hommann et al.
2008/0147006 A1   6/2008   Brunnberg et al.
(Continued)

FOREIGN PATENT DOCUMENTS

WO    2013/034984 A2    3/2013

OTHER PUBLICATIONS

International Search Report and Written Opinion for Int. App. No. PCT/EP2017/057401, dated Jul. 7, 2017.

*Primary Examiner* — Brandy S Lee
*Assistant Examiner* — Nidah M Hussain
(74) *Attorney, Agent, or Firm* — McDonnell Boehnen Hulbert & Berghoff LLP

(57) ABSTRACT

An administration mechanism for a medicament delivery device is disclosed having a linearly displaceable medicament delivery member cover, an actuator sleeve, an actuator, wherein the medicament delivery member cover is configured to axially displace the actuator sleeve from an initial position to a distally displaced position thereby displacing the actuator sleeve relative to the actuator, a rotator having a guide structure, a plunger holder, and a plunger rod that is proximally biased. The actuator can engage with the plunger holder in the initial position of the actuator sleeve to prevent the plunger holder from proximal displacement relative to the actuator. The actuator can be released from engagement with the plunger holder by displacement of the actuator sleeve towards the distally displaced position to enable proximal displacement of the plunger holder, the plunger rod and the rotator relative to the actuator. The actuator can rotate the rotator relative to the plunger holder, releasing the plunger rod from the plunger holder.

20 Claims, 7 Drawing Sheets

(58) Field of Classification Search
USPC .......................................................... 604/187
See application file for complete search history.

(56) References Cited

U.S. PATENT DOCUMENTS

| | | |
|---|---|---|
| 2013/0261558 A1 | 10/2013 | Hourmand et al. |
| 2013/0317431 A1* | 11/2013 | KraMer ............. A61M 5/2033 604/131 |
| 2014/0257193 A1* | 9/2014 | Bostrom ............. A61M 5/3204 604/197 |
| 2015/0335829 A1* | 11/2015 | Giambattista ....... A61M 5/3204 604/192 |
| 2017/0007764 A1* | 1/2017 | Saussaye ............. A61M 5/326 |

* cited by examiner

US 11,033,686 B2

ADMINISTRATION MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/057401 filed Mar. 29, 2017, which claims priority to Swedish Patent Application No. 1650673-5 filed May 18, 2016. The entire disclosure contents of these applications are herewith incorporated by reference into the present application.

TECHNICAL FIELD

The present disclosure generally relates to medical devices. In particular, it relates to an administration mechanism for a medicament delivery device, and to a medicament delivery device comprising an administration mechanism.

BACKGROUND

Medicament delivery devices such as auto-injectors may have an auto-penetration mechanism, i.e. a spring-tensed arrangement which is shifted proximally, bringing the medicament container and the medicament delivery member forward, when the medicament delivery device is activated. In order to be able to control activation of the medicament delivery device, the medicament delivery member must be prevented from being undesirably pulled forwards.

US 2008/015520 A1 discloses an auto-injector with an active agent container latching. The auto-injector has an elongated casing, in which an active agent container connected to an injection needle can be shifted axially by a spring force. At least one latching tongue prevents the active agent container from being prematurely shifted with respect to the casing, by abutting a flange arranged on a sliding sleeve which accommodates the active agent container. When the auto-injector is placed onto a person's skin, a needle protecting tube is shifted into the casing, forcing the latching tongue away from the flange and, thus, freeing the travel path for needle movement.

According to US 2008/015520 A1 the needle will not be shifted forward to such an extent that it can penetrate the application surface. Moreover, medicament expulsion will not be initiated by this backward-shifting of the needle protecting tube. This requires the user to push the triggering ring at the distal end of the device, which initiates forward movement of the piston rod, and which brings the agent container further forward. Medicament administration hence requires a two-stage user interaction procedure.

SUMMARY

In view of the above, a general object of the present disclosure is to provide an administration mechanism for a medicament delivery device which solves or at least mitigates problems of the prior art.

There is hence according to a first aspect of the present disclosure provided an administration mechanism for a medicament delivery device, comprising: a linearly displaceable medicament delivery member cover, an actuator sleeve, an actuator configured to be received by the actuator sleeve, wherein the medicament delivery member cover is configured to axially displace the actuator sleeve from an initial position to a distally displaced position thereby displacing the actuator sleeve relative to the actuator, a rotator having a guide structure and configured to be received by the actuator, a plunger holder configured to be received by and engage with the rotator, which rotator and plunger holder are configured to be proximally biased, and a plunger rod configured to be received by and engage with the plunger holder in the initial position of the actuator sleeve, which plunger rod is configured to be proximally biased, wherein the actuator is configured to engage with the plunger holder in the initial position of the actuator sleeve, thereby preventing the plunger holder from proximal displacement relative to the actuator, wherein the actuator is configured to be released from engagement with the plunger holder by displacement of the actuator sleeve towards the distally displaced position, thereby enabling proximal displacement of the plunger holder, the plunger rod and the rotator relative to the actuator, whereby the actuator is configured to engage with the guide structure of the rotator and to rotate the rotator relative to the plunger holder, releasing the plunger rod from the plunger holder.

The administration mechanism enables auto-penetration and medicament expulsion by a single user interaction, i.e. by shifting the medicament delivery member cover backwards, i.e. in the distal direction. This movement releases the proximally biased plunger holder from engagement with the actuator, and as the plunger holder is moved proximally, it eventually allows the actuator to rotate the rotator thus releasing the proximally biased plunger rod.

According to one embodiment the actuator has a flexible radially inwards extending portion configured to engage with the plunger holder in the initial position of the actuator sleeve.

According to one embodiment the plunger holder has a radial heel provided with a radial surface, and wherein in the initial position, the actuator sleeve is configured to press the flexible radially inwards extending portion radially inwards to bear against the radial surface.

According to one embodiment the radial surface is configured to be arranged distally relative to the flexible radially inwards extending portion in the initial position of the actuator sleeve, thereby preventing proximal displacement of the plunger holder.

According to one embodiment the medicament delivery member cover has a larger distance between opposite inner surfaces than the actuator sleeve has, to allow the flexible radially inwards extending portion to flex radially outwards under the medicament delivery member cover when the actuator sleeve is in the distally displaced position.

According to one embodiment the guide structure is provided on an outer surface of the rotator and includes a proximal portion defined by an axial groove portion and a contiguous distal portion defined by an inclined groove portion, wherein the flexible radially inwards extending portion is configured to run in the axial groove portion and the inclined groove portion when the actuator sleeve is in the distally displaced position.

According to one embodiment the plunger rod has a radial opening and the plunger holder has a flexible radially inwards extending tab configured to be received in the radial opening thereby preventing the plunger rod from axial displacement relative to the plunger holder.

According to one embodiment, in a pre-rotation position of the rotator, the rotator is configured to press the flexible radially inwards extending tab into the radial opening.

According to one embodiment the rotator has a window configured to align with the flexible radially inwards extending tab of the plunger holder in a post-rotation position of the rotator, thereby releasing the plunger rod from engagement with the plunger holder.

One embodiment comprises a first resilient member configured to bias the plunger holder and the rotator proximally.

One embodiment comprises a second resilient member configured to bias the plunger rod proximally.

One embodiment comprises a third resilient member configured to bias the medicament delivery member cover proximally.

There is according to a second aspect of the present disclosure provided a medicament delivery device comprising: a housing, and an administration mechanism according to the first aspect, configured to be received by the housing, wherein the medicament delivery member cover is configured to be linearly displaceable from an extended position to a retracted position relative to the housing, and wherein the medicament delivery member cover is configured to displace the actuator sleeve from the initial position to the distally displaced position when moved from the extended position to the retracted position.

According to one embodiment the actuator sleeve and the plunger holder are rotationally locked relative to the housing.

According to one embodiment the medicament delivery member cover has a radial protrusion and the housing has a radial opening for receiving the radial protrusion when the medicament delivery member cover is released from its retracted position.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with an administration mechanism, refers to that end of the administration mechanism which when mounted inside a housing of a medicament delivery device is closest to the proximal end of the medicament delivery device. The proximal end of the medicament delivery device is hence that end which is to be pointed towards the site of injection during medicament expulsion. The same considerations also apply when referring to any component of the administration mechanism. The "distal end" is the opposite end relative to the proximal end. With "proximal direction" and, equivalently, "proximally" is meant a direction from the distal end towards the proximal end, along the central axis of the cap assembly. With "distal direction" or "distally" is meant the opposite direction to "proximal direction".

Figure 1A:
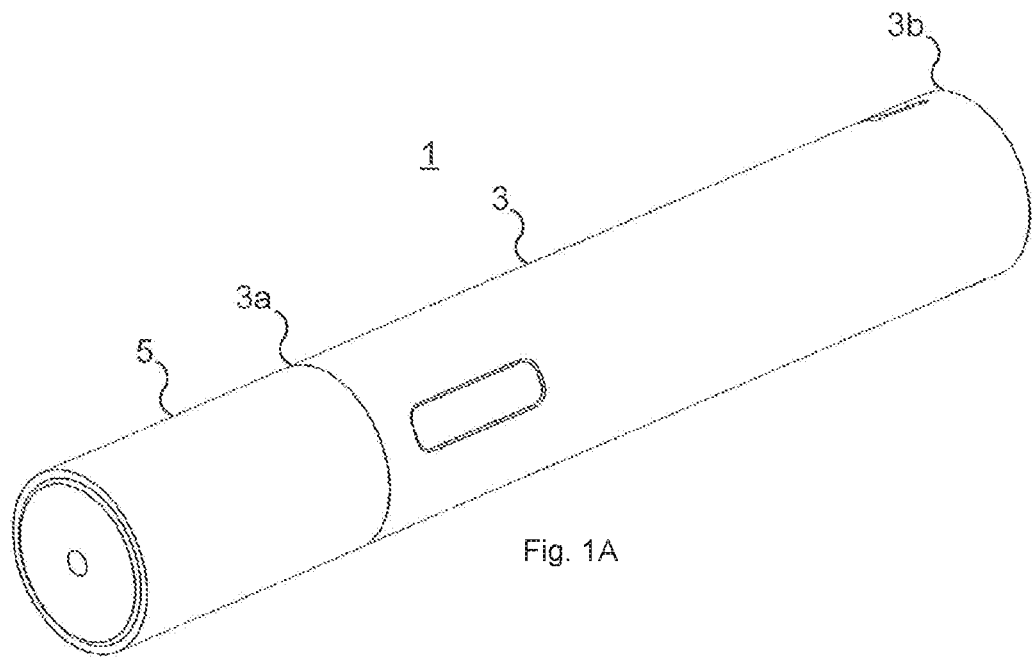
FIG. 1A is a perspective view of a medicament delivery device.

FIG. 1a shows a perspective view of an example of a medicament delivery device comprising an administration mechanism. An administration mechanism in this context is a mechanism or device which when the medicament delivery device is activated, shifts the medicament container and the medicament delivery member forward or in the proximal direction.

Medicament delivery device 1 has a housing 3 having a proximal end 3a and a distal end 3b, and a cap 5 configured to protect the medicament delivery member contained inside the housing 3. FIG. 3b shows the medicament delivery device 1 with the cap 5 removed.

Figure 1B:
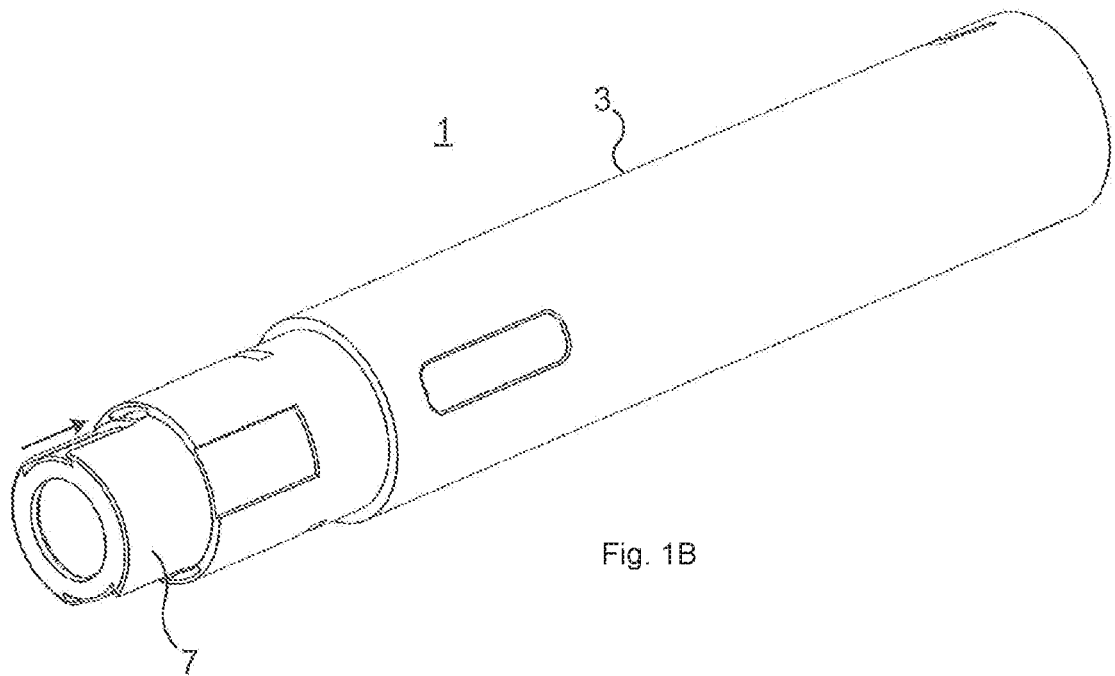
FIG. 1B is another perspective view of a medicament delivery device.

The medicament delivery device 1 also has an elongated medicament delivery member cover 7 which is linearly displaceable inside the housing 3, relative to the housing 3. The medicament delivery member cover 7 is biased in the proximal direction and movable from an initial extended position relative to the housing 3, in which position a proximal portion of the medicament delivery member cover 7 extends from the proximal end 3a of the housing 3, shown in FIG. 1b, to a retracted position. The direction of movement towards the retracted position is indicated by the arrow. Due to it being proximally biased, the medicament delivery member cover 7 is shifted or displaced proximally when the distal force is removed, thereby again obtaining an extended position relative to the housing 3. According to one variation, the medicament delivery member cover 7 is configured to engage with the housing 3 when reaching a final extended position after having been released from the retracted position. The medicament delivery member cover 7 is thus retained in the final extended position.

Figure 2:
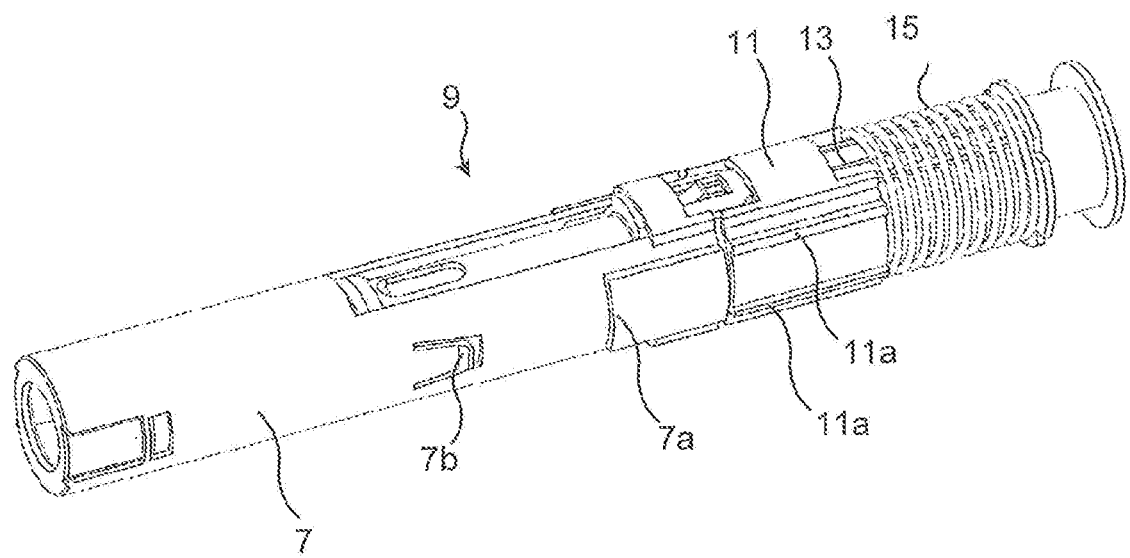
FIG. 2 is a perspective view of an example of an administration mechanism of the medicament delivery device in FIGS. 1a and 1b.

The medicament delivery device 1 also includes an administration mechanism. In FIG. 2 the housing 3 has been removed to expose an example of an administration mechanism 9 in a mounted state. The administration mechanism 9 comprises the medicament delivery member cover 7, an actuator sleeve 11, and an actuator 13 received by the actuator sleeve 11. In a mounted state, the distal end of the medicament delivery member cover 7 is aligned with the actuator sleeve 11 and arranged proximally with respect to the actuator sleeve 11. Distal displacement of the medicament delivery member cover 7 therefore displaces the actuator sleeve 11 in the distal direction. The actuator sleeve 11 and the medicament delivery member cover 7 are biased in the proximal direction. The administration mechanism 9 may thus include a resilient member 15, for example a spring, arranged distally with respect to the actuator sleeve 11. The actuator 13 may according to one variation include a distal flange 14 supporting the resilient member 15. Distal displacement of the medicament delivery member cover 7 hence moves the actuator sleeve 11 distally thereby compressing the resilient member 15. The medicament delivery member cover 7 is thus urged by the resilient member 15 towards its extended position relative to the housing 3.

The medicament delivery member cover 7 is configured to be rotationally locked relative to the housing 3. This can for example be achieved by a structure 7a provided on the outer surface of the medicament delivery member cover 7, configured to engage with a corresponding structure provided on the inner surface of the housing 3. Similarly, the actuator sleeve 11 is configured to be rotationally locked relative to the housing 3. The actuator sleeve 11 may for this purpose for example have a guide structure 11a arranged on its outer surface and configured to engage with a corresponding guide structure provided on the inner surface of the housing 3.

The medicament delivery member cover 7 may according to one variation include a radial protrusion 7b, or latch, configured to engage with the housing 3 when the medicament delivery member cover 7 returns towards the extended position from the retracted position, to thereby become axially locked relative to the housing in a final extended position. The radial protrusion 7b may extend radially outwards and be radially flexible, allowing it to slide into a recess or opening of the inner surface of the housing 3 thereby interlocking these two components.

Figure 3:
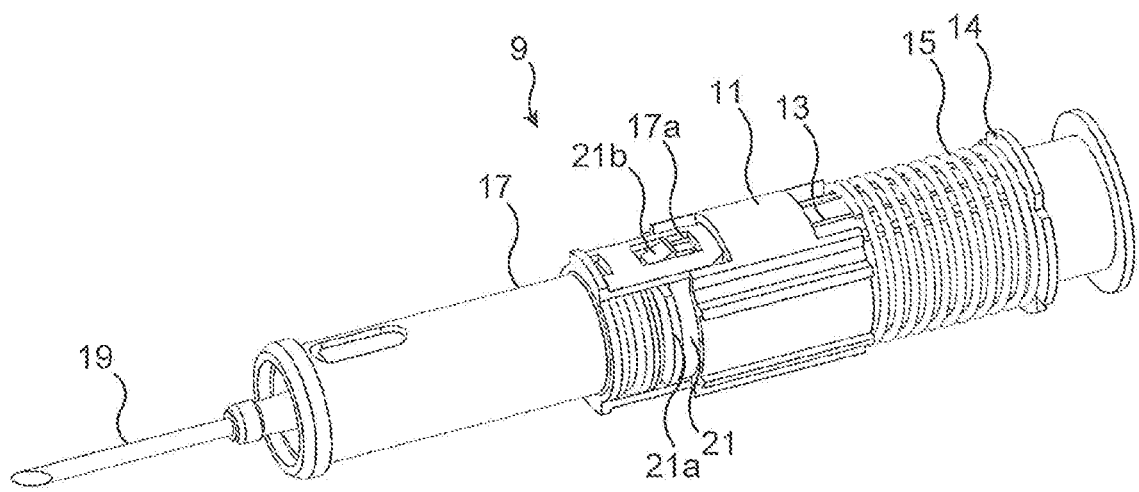
FIG. 3 shows the administration mechanism in FIG. 2 with the medicament delivery member cover removed exposing a medicament container holder.

FIG. 3 shows the arrangement in FIG. 2 with the medicament delivery member cover 7 removed to expose a proximally displaceable medicament container holder 17 configured to accommodate a medicament container provided with a medicament delivery member, such as the needle 19 shown in the present example.

The administration mechanism 9 furthermore includes a plunger holder 21 configured to be received by the actuator 13. The plunger holder 21 may be provided with a proximal flange 21a configured to bear against the medicament container arranged inside the medicament container. Proximal displacement of the plunger holder 21 hence urges the medicament container and the medicament container holder 17 in the proximal direction, providing an auto-penetration functionality.

The plunger holder 21 may also be provided with radially extending heels 21b configured to engage with corresponding openings 17a of the medicament container holder 17. The plunger holder 21 and the medicament container holder 17 are hence axially interlocked with each other so that axial displacement in the distal direction of the plunger holder 21 also results in a corresponding distal displacement of the medicament container holder 17.

Figure 4:
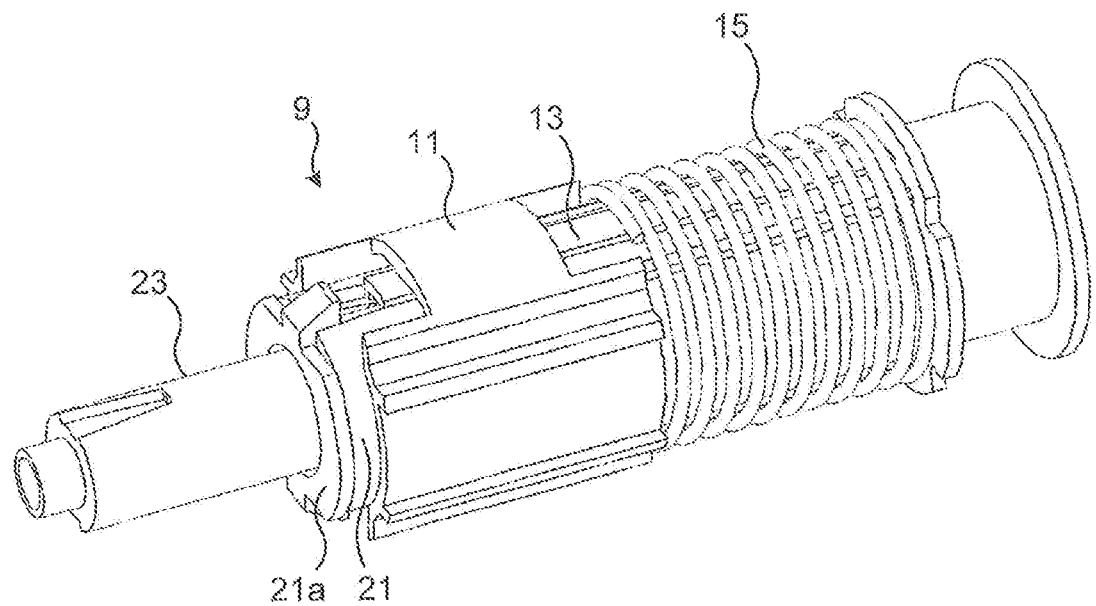
FIG. 4 shows perspective view of certain components of the administration mechanism in FIG. 2.

FIG. 4 shows the administration mechanism 9 with the medicament container holder 17 removed. The exemplified administration mechanism 9 further comprises an elongated plunger rod 23 arranged in the plunger holder 21, and a rotator not shown in FIG. 4. Hereto, the actuator sleeve 11, the actuator 13, the rotator, the plunger holder 21 and the plunger rod 23 are arranged concentrically in the listed order, with the actuator sleeve 11 being arranged radially outermost and the plunger rod 23 radially innermost.

Figure 5:
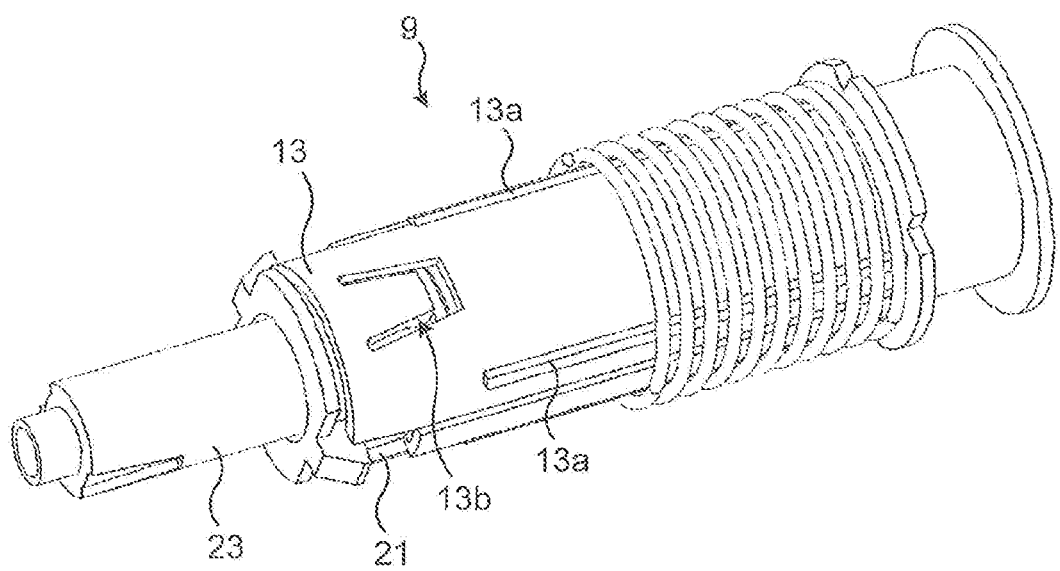
FIG. 5 shows a perspective view of certain components of the administration mechanism in FIG. 2.

FIG. 5 shows the administration mechanism 9 without the actuator sleeve 11, exposing the actuator 13. The actuator sleeve 11 and the actuator 13 are rotationally locked relative to each other. Since the actuator sleeve 11 is configured to be rotationally locked relative to the housing 3, the actuator 13 is also rotationally locked relative to the housing 3. The actuator sleeve 11 and the actuator 13 are however configured to be axially displaceable relative to each other. The actuator 13 may thus for example comprise one or more axial ribs 13a configured to engage with corresponding grooves of the actuator sleeve 11. Relative axial displacement may thereby be provided while preventing relative rotation between these components.

The actuator 13 has a flexible radially inwards extending portion 13b, a latch. This flexible radially inwards extending portion 13b is prevented from flexing radially outwards by the inner surface of the actuator sleeve 11 when the actuator sleeve 11 is in its initial position. In particular, the inner surface of the actuator sleeve 11 bears against the flexible radially inwards extending portion 13b such that the portion 13b bears against a radial surface of the plunger holder 21 in the initial extended position of the medicament delivery member cover 7, as will be explained in more detail in the following.

Figure 6:
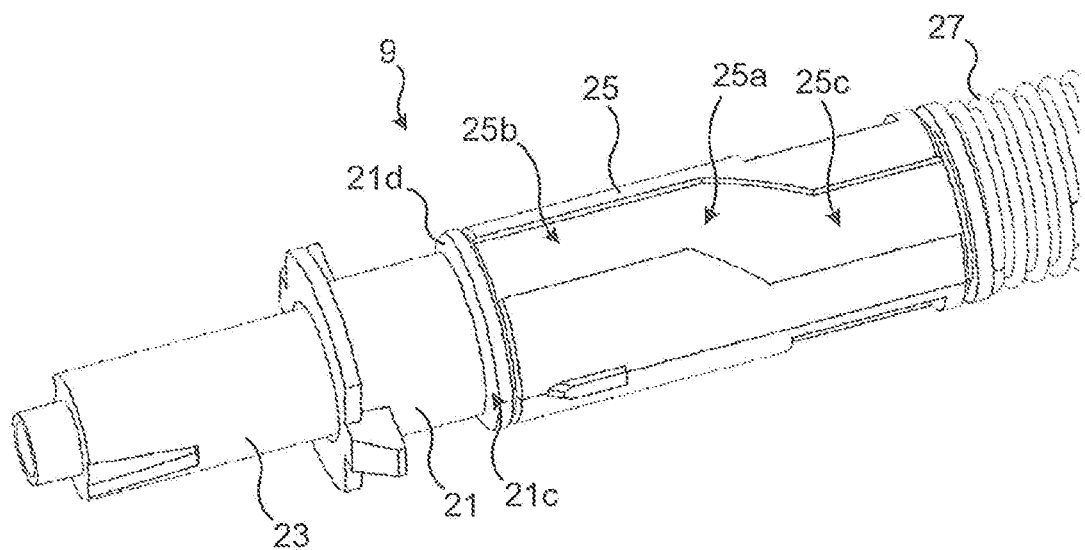
FIG. 6 shows an additional component of the administration mechanism in FIG. 2.

In FIG. 6, the actuator 13 has been removed to expose the rotator 25 which is arranged around the plunger holder 21 and to show a proximal portion of the plunger holder 21. The plunger holder 21 has a radially extending heel 21c, according to the present example a flange, having a radial surface 21d. The flexible radially inwards extending portion 13b bears against this radial surface 21d in the initial extended position of the medicament delivery member cover 7. The radial surface 21d is arranged distally relative to the flexible radially inwards extending portion 13b in the initial extended position of the medicament delivery member cover 7. Moreover, the plunger holder 21 is proximally biased by another resilient member 27, arranged inside the actuator. The radial surface 21d prevents the plunger holder 21 from proximal displacement due to the biasing, as long as the flexible radially inwards extending portion 13b bears against the radial surface 21, i.e. as long as the actuator sleeve 11 prevents the flexible radially inwards extending portion 13b from flexing radially outwards.

The rotator 25 bears against a distal surface of the radial heel 21c, or flange, which prevents the rotator 25 from independently moving proximally relative to the plunger holder 21. The rotator 25 is also proximally biased. In particular, the rotator 25 is proximally biased by resilient member 27.

The rotator 25 has a guide structure 25a provided on an outer surface thereof. The guide structure 25a includes a proximal portion 25 defined by an axial groove portion and a contiguous proximal portion 25b defined by an inclined groove portion. The inclined groove portion is inclined with respect to a plane extending through the centre of the rotator 25 and parallel with the axial groove portion. The guide structure 25a, in particular the axial groove portion and the inclined groove portion are dimensioned to receive the flexible radially inwards extending portion 13b, which when having released the plunger holder 21 due to radial outwards flexing, will slide into the proximal portion 25b of the guide structure 25a. As the rotator 25 is moved in the distal direction by resilient member 27, the flexible radially inwards extending portion 13b will reach the inclined groove portion, forcing the rotator 25 to rotate.

Figure 7:
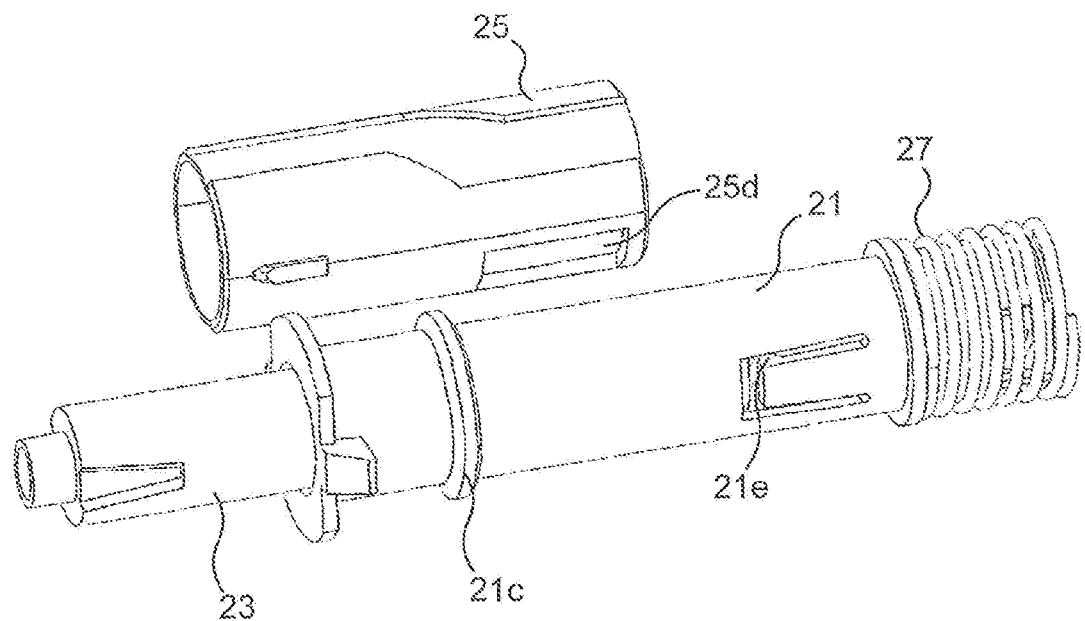
FIG. 7 shows an additional component of the administration mechanism in FIG. 2.
Figure 8:
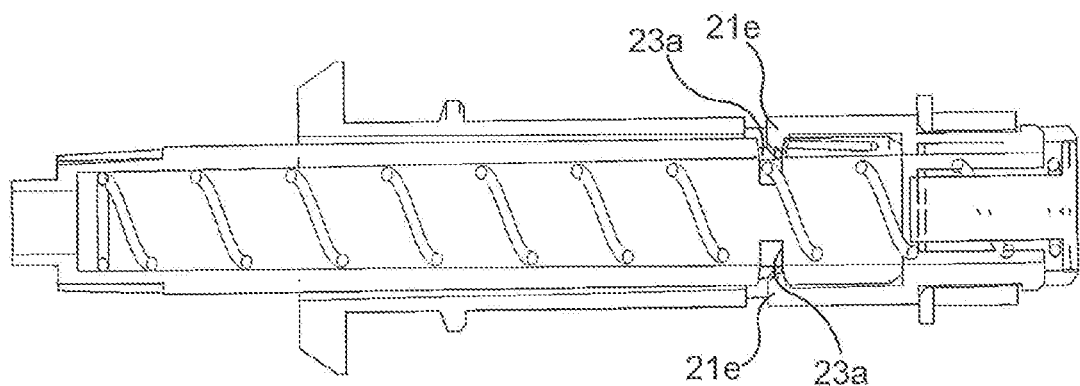
FIG. 8 is a longitudinal section of a plunger holder and plunger rod of the administration mechanism, the section being at right angle to the longitudinal section in FIG. 8.

In FIG. 7, the rotator 25 has been moved away from the plunger holder 21 to expose the plunger holder 21. The plunger rod 23 is configured to be proximally biased by yet another resilient member 29 as shown in FIG. 8. This resilient member 29 is arranged inside the hollow plunger rod 23. The plunger holder 21 is configured to initially engage with the plunger rod 23 to prevent the plunger rod 23 from axial displacement in the proximal direction. Hereto, according to one variation the plunger holder 21 has one or more flexible radially inwards extending tab(s) 21e configured to engage with a corresponding radial opening(s) 23a of the plunger rod 23, as shown in FIG. 8. The inner surface of the rotator 25 is configured to prevent the flexible radially inwards extending tab 21e from flexing radially outwards so that it engages with the radial opening 23a of the plunger rod 23.

The rotator 25 may according to one variation be provided with a window 25d, i.e. an opening configured to align with the flexible radially inwards extending tab 21e when the rotator is rotated. The flexible radially inwards extending tab 21e will thereby be allowed to flex radially as a result of the proximally directed force provided by the resilient member 29. The plunger rod 23 is thereby released from its engagement with the plunger holder 21 allowing it to move proximally so that medicament expulsion may be commenced.

Figure 9A:
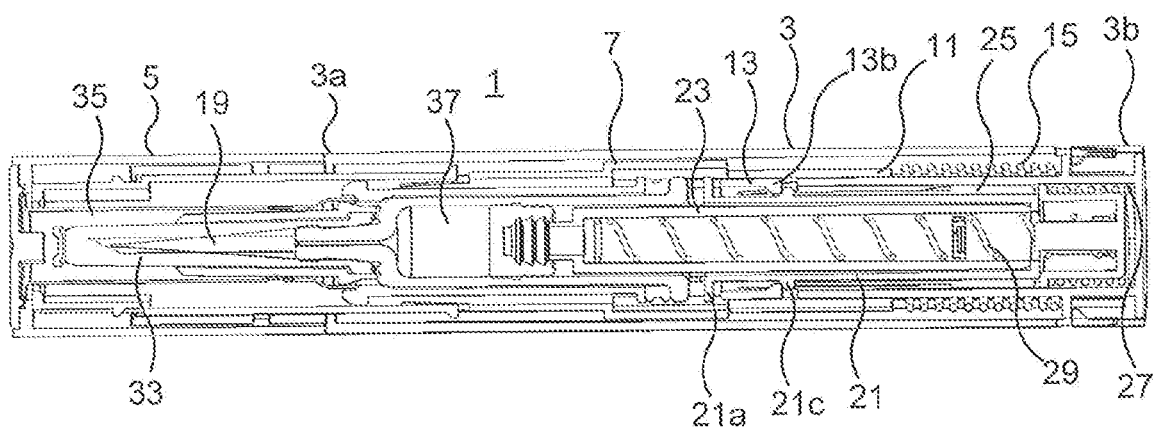
FIG. 9A shows longitudinal sections of the medicament delivery device in FIG. 1 in a different stage of operation.

FIG. 9a shows a longitudinal section of the medicament delivery device 1 in an initial state in which the cap 5 is positioned proximally relative to the housing 3 to protect the internal components of the medicament delivery device 1. In this position, a number of components are biased in the proximal direction. In particular resilient member 27, termed a first resilient member, is configured to bias the plunger holder 21 and the rotator 25 proximally, resilient member 29, termed a second resilient member, is configured to bias the plunger rod 23 proximally, and resilient member 15, termed a third resilient member, is configured to bias the medicament delivery member cover 7 proximally. According to the present example, each resilient member 15, 27, 29 is a spring.

The exemplified medicament delivery device 1 accommodates a medicament container 37, a medicament delivery member in the form of a needle 19, and a medicament delivery member shield 33, i.e. a needle shield. The cap 5 is provided with a medicament delivery member shield remover 35 for removing the medicament delivery member shield 33 when the cap 5 is removed.

Figure 9B:
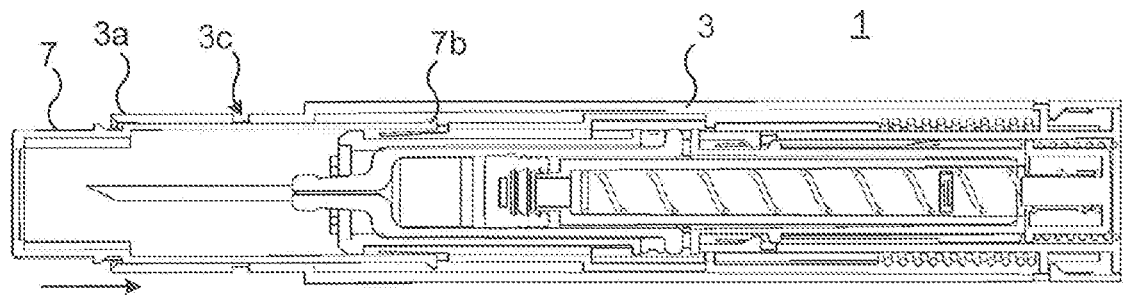
FIG. 9B shows a longitudinal section of the medicament delivery device in FIG. 1 in a different stage of operation.

Turning now to FIG. 9b, the medicament delivery device 1 is again in the initial position, however with the cap 5 removed. The medicament delivery member shield 33 has thus been removed by the medicament delivery member shield remover 35. The medicament delivery member cover 7 extends from the proximal end 3a of the housing 3, and is arranged in the extended position. Moreover, the actuator sleeve 11 is arranged in its initial position. In this state, the medicament delivery device 1 is ready for injection, activation being initiated by fully pushing the medicament delivery member cover 7 distally into the housing 3, the direction being indicated by the arrow.

It may further be noted that in the initial extended position of the medicament delivery member cover 7 shown in FIG. 9b the radial protrusion 7b is arranged distally relative to an opening 3c in the housing 3. The opening 3c is arranged to receive the radial protrusion 7b when the third resilient member 15 is expanded after the user has released the medicament delivery member cover 7 from its retracted position.

Figure 9C:
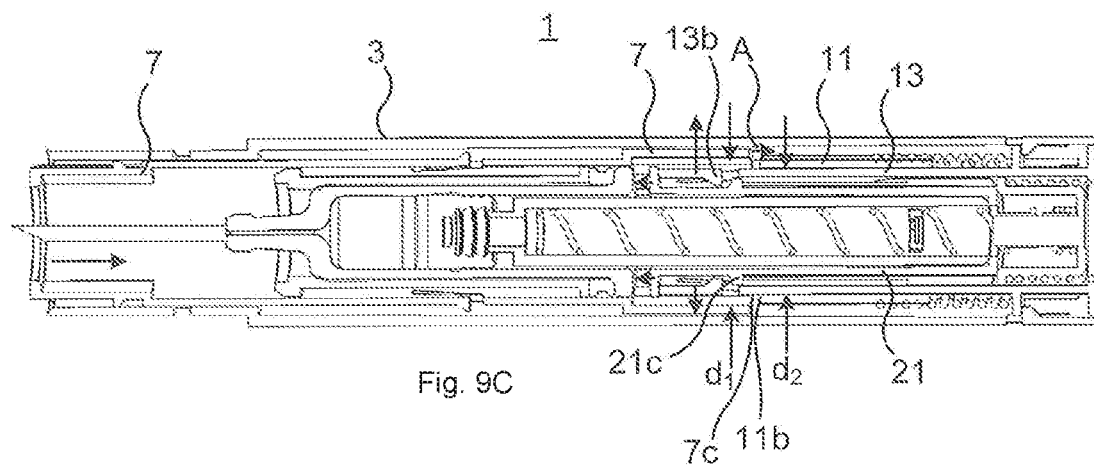
FIG. 9C shows a longitudinal section of the medicament delivery device in FIG. 1 in a different stage of operation.

In FIG. 9c the medicament delivery member cover 7 has been pushed distally into the housing 3. The medicament delivery member cover 7 has hence been moved linearly inside 12 the housing 3, as shown by arrow A The distal end 7c of the medicament delivery member cover 7 is thereby brought towards and into contact with the proximal end of the 11b of the actuator sleeve 11, thereby displacing the actuator sleeve 11 in the distal direction. The actuator sleeve 11 has an inner dimension $d_2$, namely the distance between two opposite inner surfaces which prevent the flexible radially inwards extending portion 13b of the actuator 13 from flexing radially outwards, which is smaller than the corresponding inner dimension $d_1$ of the medicament delivery member cover 7. Hereto, when the actuator sleeve 11 has been displaced sufficiently far distally by the medicament delivery member cover 7, the medicament delivery member cover 7 will enclose, or be axially aligned with, the flexible radially inwards extending portion 13b. Because of the larger inner dimension $d_2$ of the medicament delivery member cover 7, the flexible radially inwards extending portion 13b is allowed to flex radially outwards as it is being urged by the proximally biased plunger holder 21, in particular the radial heel 21c thereof, as symbolically illustrated by the radial arrows. In this manner, the radial heel 21c, or flange, is allowed to pass underneath the flexible radially inwards extending portions 13b, or portions 13b as there are two such portions in the example shown in the drawings, distributed at about 180 degrees in the circumferential direction. The plunger holder 21 is thus released from being axially interlocked with the actuator 13, and moved proximally due to the proximal force exerted by the first resilient member 27.

Figure 9D:
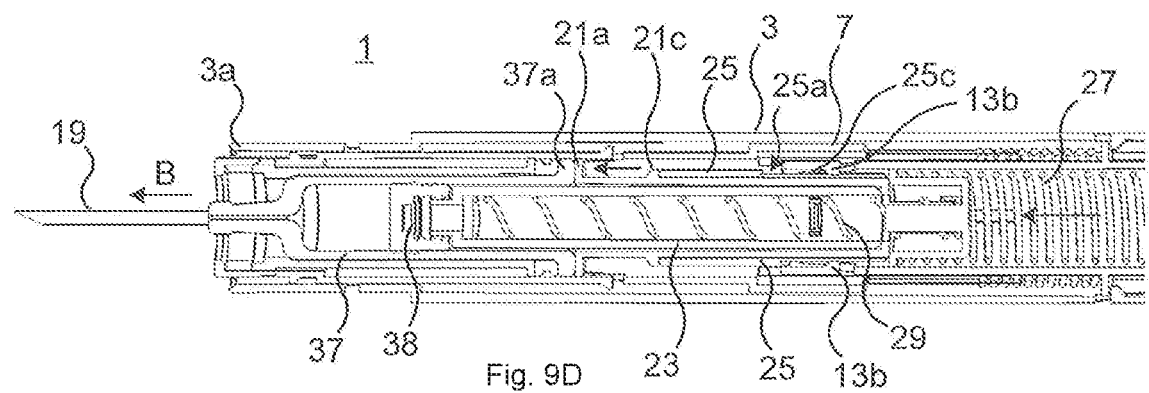
FIG. 9D shows a longitudinal section of the medicament delivery device in FIG. 1 in a different stage of operation.

Turning now to FIG. 9d, it can be seen that the radial heel 21c, or flange, has been allowed to pass by the flexible radially inwards extending portion 13b in the proximal direction as the plunger holder 21 and the rotator 25 are moved proximally. The flexible radially inwards extending portion 13b is hence moved into the guide structure 25a, of which the distal portion 25c is visible in FIG. 9d. The flexible radially inwards extending portion 13b is hence moved in the guide structure 25a, from the proximal portion into the distal portion 25c as the rotator 25 and the plunger holder 21 move proximally. As previously mentioned, the plunger holder 21 is configured to displace the medicament container 37 proximally since the proximal flange 21a of the plunger holder 21 bears against a distal flange 37a of the medicament container 37. The proximal movement of the medicament container 37 and the needle 19 relative to the housing 3 is illustrated by the arrow B.

The axial length of the proximal portion 25b of the guide structure 25a determines the amount that the plunger holder 21 is moved proximally and thus the amount that the medicament container 37 is moved proximally before medicament expulsion can commence. The axial length may in particular be dependent on a particular application of the medicament delivery device 1. According to the present example, the medicament container 37 is moved proximally to such an extent that the needle 19 is shifted proximally to extend fully beyond the proximal end 3a of the housing 3.

When the flexible radially inwards extending portion 13b moves into the distal portion 25c, the rotator 25 is rotated, since the actuator 13 is rotationally locked relative to the housing 3. When the rotator is rotated, the window 25d is aligned with the flexible radially inwards extending tab 21e. The flexible radially inwards extending tab 21e will thereby be allowed to flex radially as a result of the proximally directed force provided by the resilient member 29.

The plunger rod 23 is thereby released from its engagement with the plunger holder 21, allowing it to move proximally as a result from it being biased proximally by the resilient member 29. Upon being released from engagement with the plunger holder 21, the plunger rod 23 is configured to proximally displace a plunger 38 arranged in the medicament container 37, and to move it proximally until the entire dose of medicament has been expelled through the needle 19.

Figure 9E:
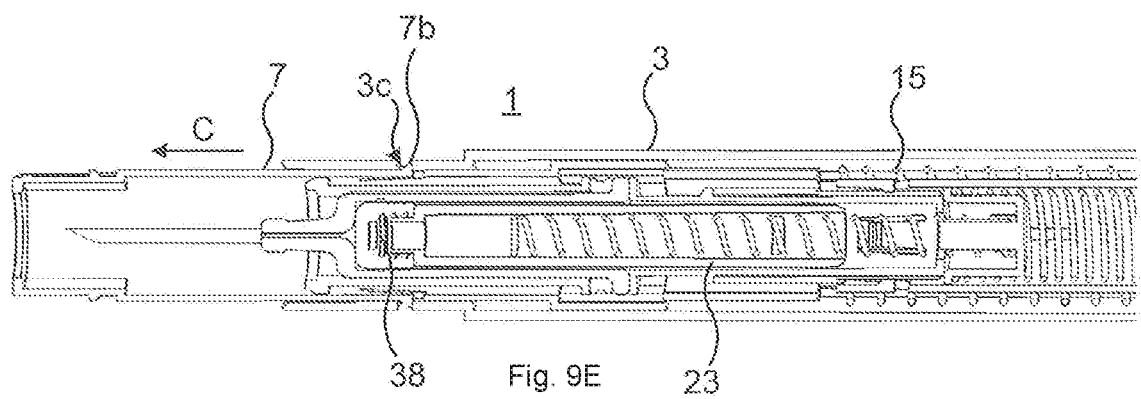
FIG. 9E shows a longitudinal section of the medicament delivery device in FIG. 1 in a different stage of operation.

FIG. 9e shows the medicament delivery device 1 when the medicament delivery member cover 7 has been released so that the expansion of the resilient member 15 moves the medicament delivery member cover 7 in the proximal direction, as shown by arrow C to a final extended position. The medicament delivery member cover 7 is hence moved proximally until the radial protrusion 7b engages with the opening 3c of the housing 3. The medicament delivery member cover 7 will thereby interlock with the housing 3 and is thus prevented from being subsequently being moved distally towards the retracted position. The used needle 19 will thus be covered by the medicament delivery member cover 7 ensuring anyone handling the used medicament delivery device 1 from being pierced by it.

The administration mechanism disclosed herein may for example be utilised in a medicament delivery device that is an auto-injector. The medicament delivery device may be of a disposable, single-use type, or it may be of a type that allows multiple doses to be administered.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An administration mechanism for a medicament delivery device, comprising:
 a linearly displaceable medicament delivery member cover,
 an actuator sleeve,
 an actuator configured to be received by the actuator sleeve,
 wherein the medicament delivery member cover is configured to axially displace the actuator sleeve from an initial position to a distally displaced position thereby displacing the actuator sleeve relative to the actuator,
 a rotator having a guide structure and configured to be received by the actuator,
 a plunger holder configured to be received by and engage with the rotator, which rotator and plunger holder are configured to be proximally biased, and
 a plunger rod configured to be received by and engage with the plunger holder in the initial position of the actuator sleeve, which plunger rod is configured to be proximally biased,
 wherein the actuator is configured to engage with the plunger holder in the initial position of the actuator sleeve, thereby preventing the plunger holder from proximal displacement relative to the actuator,
 wherein the actuator is configured to be released from engagement with the plunger holder by displacement of the actuator sleeve towards the distally displaced position, thereby enabling proximal displacement of the plunger holder, the plunger rod and the rotator relative to the actuator, whereby the actuator is configured to engage with the guide structure of the rotator and to rotate the rotator relative to the plunger holder, releasing the plunger rod from the plunger holder.

2. The mechanism as claimed in claim 1, wherein the actuator has a flexible radially inwards extending portion configured to engage with the plunger holder in the initial position of the actuator sleeve.

3. The mechanism as claimed in claim 2, wherein the plunger holder has a radial heel provided with a radial surface, and wherein in the initial position, the actuator sleeve is configured to press the flexible radially inwards extending portion radially inwards to bear against the radial surface.

4. The mechanism as claimed in claim 3, wherein the radial surface is configured to be arranged distally relative to the flexible radially inwards extending portion in the initial position of the actuator sleeve, thereby preventing proximal displacement of the plunger holder.

5. The mechanism as claimed in claim 2, wherein the medicament delivery member cover has a larger distance between opposite inner surfaces than the actuator sleeve has, to allow the flexible radially inwards extending portion to flex radially outwards under the medicament delivery member cover when the actuator sleeve is in the distally displaced position.

6. The mechanism as claimed in claim 2, wherein the guide structure is provided on an outer surface of the rotator and includes a proximal portion defined by an axial groove portion and a contiguous distal portion defined by an inclined groove portion, wherein the flexible radially inwards extending portion is configured to run in the axial groove portion and the inclined groove portion when the actuator sleeve is in the distally displaced position.

7. The mechanism as claimed in claim 1, wherein the plunger rod has a radial opening and the plunger holder has a flexible radially inwards extending tab configured to be received in the radial opening thereby preventing the plunger rod from axial displacement relative to the plunger holder.

8. The mechanism as claimed in claim 7, wherein in a pre-rotation position of the rotator, the rotator is configured to press the flexible radially inwards extending tab into the radial opening.

9. The mechanism as claimed in claim 8, wherein the rotator has a window configured to align with the flexible radially inwards extending tab of the plunger holder in a post-rotation position of the rotator, thereby releasing the plunger rod from engagement with the plunger holder.

10. The mechanism as claimed in claim 1, comprising a first resilient member configured to bias the plunger holder and the rotator proximally.

11. The mechanism as claimed in claim 1, comprising a second resilient member configured to bias the plunger rod proximally.

12. The mechanism as claimed in claim 1, comprising a third resilient member configured to bias the medicament delivery member cover proximally.

13. A medicament delivery device comprising:
 a housing, and an administration mechanism as claimed in claim 1, configured to be received by the housing, wherein the medicament delivery member cover is configured to be linearly displaceable from an extended position to a retracted position relative to the housing, and wherein the medicament delivery member cover is configured to displace the actuator sleeve from the initial position to the distally displaced position when moved from the extended position to the retracted position.

14. The medicament delivery device as claimed in claim 13, wherein the actuator sleeve and the plunger holder are rotationally locked relative to the housing.

15. The medicament delivery device as claimed in claim 13, wherein the medicament delivery member cover has a radial protrusion and the housing has a radial opening for receiving the radial protrusion when the medicament delivery member cover is released from its retracted position.

16. The medicament delivery device of claim 13 wherein the plunger rod has a radial opening and the plunger holder has a flexible radially inwards extending tab configured to be received in the radial opening thereby preventing the plunger rod from axial displacement relative to the plunger holder.

17. The medicament delivery device of claim 13 further comprising:
- a first resilient member configured to bias the plunger holder and the rotator proximally;
- a second resilient member configured to bias the plunger rod proximally; and
- a third resilient member configured to bias the medicament delivery member cover proximally.

18. An administration mechanism for a medicament delivery device, comprising:
- a linearly displaceable medicament delivery member cover;
- an actuator sleeve;
- an actuator received by the actuator sleeve;
- a rotator received in the actuator and comprising a guide structure;
- a plunger holder engaged with the rotator, where both the rotator and plunger holder are proximally biased by a resilient member; and
- a plunger rod located within and engaged with the plunger holder when the actuator sleeve is in an initial position, where the plunger rod is biased proximally by a second resilient member, wherein when the medicament delivery member cover moves distally it axially displaces the actuator sleeve from an initial position to a distally displaced position causing displacement of the actuator sleeve relative to the actuator, wherein when the actuator sleeve is in the initial position, the actuator is engaged with the plunger holder preventing the resilient member from moving the plunger holder proximally, wherein the actuator is released from engagement with the plunger holder by displacement of the actuator sleeve towards the distally displaced position which causes proximal displacement of the plunger holder, the plunger rod and the rotator relative to the actuator, and wherein the actuator is configured to engage with the guide structure to rotate the rotator relative to the plunger holder to release the plunger rod from the plunger holder.

19. The medicament delivery device of claim 18, wherein the plunger rod has a radial opening and the plunger holder has a flexible radially inwards extending tab received in the radial opening to prevent the second resilient member from moving the plunger rod axially relative to the plunger holder.

20. The medicament delivery device of claim 18, wherein the actuator has a flexible radially inwards extending portion that engages the plunger holder in the initial position, where the plunger holder has a radial heel provided with a radial surface, and where when the actuator sleeve is in the initial position, the actuator sleeve presses the flexible radially inwards extending portion radially inwards to bear against the radial surface.

\* \* \* \* \*